(12) United States Patent
Thomas

(10) Patent No.: US 8,906,894 B1
(45) Date of Patent: *Dec. 9, 2014

(54) METHODS FOR PREVENTING AND TREATING THROMBOTIC DISORDERS

(76) Inventor: Thomas N. Thomas, Palm Harbor, FL (US)

( * ) Notice: Subject to any disclaimer, the term of this patent is extended or adjusted under 35 U.S.C. 154(b) by 832 days.

This patent is subject to a terminal disclaimer.

(21) Appl. No.: 12/357,816

(22) Filed: Jan. 22, 2009

Related U.S. Application Data

(63) Continuation-in-part of application No. 10/802,000, filed on Mar. 16, 2004, now Pat. No. 8,519,005, which is a continuation-in-part of application No. 09/881,199, filed on Jul. 27, 2000, now Pat. No. 6,432,991, and a continuation-in-part of application No. 10/137,342, filed on May 3, 2002, now Pat. No. 6,635,667.

(51) Int. Cl.
*A01N 43/00* (2006.01)
*A61K 31/33* (2006.01)

(52) U.S. Cl.
USPC ............................. 514/183; 514/365

(58) Field of Classification Search
None
See application file for complete search history.

(56) References Cited

U.S. PATENT DOCUMENTS

| | | | |
|---|---|---|---|
| 6,071,514 A | 6/2000 | Grinnell et al. | |
| 6,432,991 B1 * | 8/2002 | Thomas | 514/365 |
| 6,635,667 B2 * | 10/2003 | Thomas | 514/365 |
| 7,285,530 B2 | 10/2007 | Lucas | |
| 2003/0109543 A1 | 6/2003 | Ogletree | |
| 2005/0020631 A1 * | 1/2005 | Gogliotti et al. | 514/320 |
| 2006/0122115 A1 | 6/2006 | Lucas | |
| 2006/0222640 A1 | 10/2006 | Reilly et al. | |
| 2008/0000801 A1 | 1/2008 | Mackie, Jr. | |
| 2009/0118503 A1 * | 5/2009 | Sprott et al. | 544/143 |

OTHER PUBLICATIONS

Yeh et al., Journal of Thrombosis & Haemostasis, (Nov. 2006), 4(11), pp. 2308-2316.*
Trost et al., Critical Care Medicine, (Oct. 2011), 39(10), pp. 2346-2353.*
Kinoshenko et al., Vrach. Delo., (Jan. 1989), (1), pp. 27-29 (Abstract).*
Meadows, T. A. and Bhatt, D. L. May 11, 2007. "Clinical Aspects of Platelet Inhibitors and Thrombus Formation." Cir. Res. vol. 100. pp. 1261-1275.
Ohlmann, P., Eckly, A., Freund, M., Cazenave, J., Offermanns, S., and Gachet. 2000. "ADP Induces Partial Platelet Aggregation Without Shape Change and Potentiates Collagen-Induced Aggregation in the Absence of Gaq." Blood. Sep. 15, 2000. vol. 96. No. 6. pp. 2134-2139.

(Continued)

*Primary Examiner* — San-Ming Hui
*Assistant Examiner* — Andrew Lee
(74) *Attorney, Agent, or Firm* — Robert J. Varkonyi; Smith & Hopen, P.A.

(57) ABSTRACT

Compositions and methods for anti-thrombotic and antiplatelet therapy in a subject are provided. Administration of an MAO-B inhibitor results in reduced platelet aggregation or reversion of platelet aggregation. Methods of administering an MAO-B inhibitor with at least one antiplatelet agent are also disclosed. Such combination therapies result in an additional protective effect, and in some instances a synergistic effect. The compositions and methods of the present invention are useful for treating and preventing recurrence of several cardiovascular, cerebrovascular and peripheral vascular diseases and injuries, and may be applied to subjects displaying traditional drug resistances.

13 Claims, 10 Drawing Sheets

(56) References Cited

OTHER PUBLICATIONS

Barrett, NE., Holbrook, L., Jones, S., Kaiser, WJ., Moraes, LA., Rana, R., Sage, T., Stanley, RG., Tucker, KL, Wright, B., and Gibbins, JM. 2008. "Future Innovation in Anti-Platelet Therapies." Brtish Jounal of Pharmacology. vol. 154. pp. 918-939.
Coller, BS, Beer, JH, Scudder, LE, and Steinberg, MH. Jul. 1989. Collagen-Platelet Interactions: Evidence for a Direct Interaction of Collagen with Platelet GPIa/IIa and an Indirect Interaction with Platelet GPIIa/111q Mediated by Adhesive Proteins. Blood. vol. 74. pp. 182-192.
Thomas, T., RHODIN, J., Clark, L., and Garces, A. Dec. 2003. "Progestins Initiate Adverse Events of Menopausal Estrogen Therapy." Climacteric. vol. 6. pp. 293-301.
Toyoda, K., Yasaka, M., Iwade, K. Nagata, K., Koretsune, Y., Sakamoto, T., Uchiyama, Gotoh, J., Nagao, T., Yamamoto, M., Takahashi, J.C., and Minematsu, K. Jun. 2008. "Dual Antithrombotic Therapy Increases Severe Bleeding Events in Patients with Stroke and Cardiovascular Disease." Stroke. vol. 39. pp. 1740-1745.
Cattaneo M. Nov. 2004 "Asprin and Clopidogrel Efficacy Safety, and the Issue of Dug Resisance" Arterioscler Thromb Vasc Biol. vol. 24. pp. 1980-1987.
Mackman, Nigel. Feb. 21, 2008. "Triggers, Targets and Treatments for Thrombosis." Nature. vol. 451. pp. 914-918.
Patrono, C., and Rocca, B. Mar. 2008. "Aspirin: Promise and Resistance in the New Millennium." Arterioscler Thromb Vasc Biol. vol. 28. pp. s25-s32.
Thomas, T., Sutton, E.T., Bryant, M.W., and Rhodin, J.A.G. Jul. 1997. In Vivo Vascular Damage, Leukocyte Activation and Inflammatory Response Induced by B-Amyloid. J. Submicrosc. Cytol. Pathol. vol. 29 (3). pp. 293-304.
Rhodin, J. A., and Thomas, T. Aug. 2001. "A Vascular Connection to Alzheimer's Disease." Miceocirculation. vol. 8. pp. 207-220.
Donnan, G. A., Fisher, M., Macleod, M. and Davis, S.M. May 10, 2008. "Stroke." Lancet. vol. 371. pp. 1612-1623.
Angiolillo, D. J., Guzman, L. A. and Bass, T. A. Aug. 2008. "Current Antiplatelet Therapies: Benefits and Limitations." Am. Heart. vol. 156. pp. s3-s9.
Angiolillo, D. J., and Capranzano, P. 2008. "Pharmacology of Emerging Novel Platelet Inhibitors." Am Heart J. vol. 156. pp. s10-s15.
Sprigg, N., Gray, L. J., England, T., Willmot, M.R., Zhau, L., Sare, G.M., and Bath, P.M.W. Aug. 6, 2008. "A Randomised Controlled Trial of Triple Antiplatelet Therapy (Aspirin, Clopidogrel, and Dipyridamole) in the Secondary Prevention of Stroke: Safety, Tolerability and Feasibility." PLoS One. vol. 3. Issue 8. pp. 1-6.
"New Drug Protects Against Second Heart Attack or Stroke, Study Suggests." Science Daily. http://www.sciencedaily.com/releases/2008/09/080902074559.htm. Sep. 5, 2008.
Thomas, T., Bhavnani, R., and Thomas, P. Mar. 2002. "Inhibition of Human LDL Oxidation by the Neuroprotective Drug I-Deprenyl." Neurol Res. vol. 24. pp. 169-173.
Freedman, J E. Mar. 2008. "Oxidative Stress and Platelets." Arterioscler Thromb Vasc Biol. vol. 28. pp. s11-s16.
Angiolillo, D. J., and Bates, E. R. Aug. 2008. "Platelet Inhibitor Therapy: Current Perspectives and Emerging Novel Agents: Introduction." Am Heart J. vol. 156. pp. s1-s2.
Collet, J., Hulot, J., Pena, A., Villard, E., Esteve, J., Silvain, J., Pavot, L., Brugier, D., Cayla, G., Beygui, F., Bensiman, G., Funck-Brentano, C., and Montalescot. Jan. 24, 2008. "Cytochrome P450 2C19 Polymorphism in Young Patients Treated with Clopidogrel After Myocardial Infarction: A Cohen Study." Lancelet. pp. 1-9.
Wang, S. S. Dec. 24, 2008. "Gene Variant Reduces Effectiveness of Plavix." Wall Street Journal. http://online.wsj.com/article/SB123007939192331815.html. pp. D3.
Yamamoto et al. 2010. "Gastroduodental Mucosal Injury in Patients Taking Low-Dose Aspirin and the Role of Gastric Mucoprotective Drugs: Possible Effect of Rebamipide." J. Clin. Biochem. vol. 47. pp. 27-31.
Holmes et al. 2011. CYP2C19 Genotype, Clopidogrel Metabolism, Platelet Function, and Cardiovascular Events. JAMA. vol. 306. No. 24. pp. 2704-2715.
Agewall et al. 2010. "Oral Antiplatelet Agents in ACS: From Pharmacology to Clinical Differences." Fundamental & Clinical Pharmacology. vol. 25. pp. 564-571.
Dai et al. 2012. "Clinical Use of Aspirin in Treatment and Prevention of Cardiovascular Disease." Thrombosis. vol. 2012. Article ID: 245037. pp. 1-7.
Michaelson. 2011. "Advances in Antiplatelet Therapy." American Society of Hematology. pp. 62-69.
Roe et al. 2010. "A New Era in Secondary Prevention after Acute Coronary Syndrome." The New England Journal of Medicine. pp. 1-3.
Di Minno et al. 2011. "Overcoming Limitations of Current Antiplatelet Drugs: A Concerted Effort for More Profitable Strategies of Intervention." Annals. of Medicine. vol. 43. pp. 531-544.
Roth. 2011. Nonsteriodal Anti-Inflammatory Drug Gastropathy: New Avenues for Safety. Clinical Interventions in Aging. vol. 6. pp. 125-131.
Espinosa et al. 2012. "Aspirin: Pharmacology and Clinical Applications." Thrombosis. vol. 2012. Article ID: 173124. pp. 1-15.
Musallam et al. 2011. "Resistance to Aspirin and Clopidogrel Therapy." Int. Jnl. Lab. Hem. vol. 33. pp. 1-18.
Tziros et al. 2006. "The Many Antithrombotic Actions of Nitric Oxide." Current Drug Targets. vol. 7. pp. 1243-1251.
Loscalzo. 2001. "Nitric Oxide Insufficiency, Platelet Activation, and Arterial Thrombosis." Circulation Research. vol. 88. pp. 756-762.
Coccheri. 2011. "Antiplatelet Therapy: Controversial Aspects." Thromb. Res. pp. 1-5.
Thygesen, et al.; "Universal Definition of Myocardial Infarction"; Circulation; vol. 116, pp. 2634-2653; 2007.
Van Der Schyf, et al.; "Multifunctional Drugs with Different CNS Targets for Neuropsychiatric Disorders"; Journal of Neurochemistry; vol. 99, pp. 1033-1048; 2006.
Yogev-Falach, et al.; "The Importance of Propargylamine Moiety in the Anti-Parkinson Drug Rasagiline and its Derivatives in MAPK-Dependent Amyloid Precursor Protein Processing"; The FASEB Journal; vol. 17, pp. 2325-2327, (Dec. 2003).
Erik Lerkevang Grove, Antiplatelet effect of aspirin in patients with coronary artery disease. Danish Medical Journal, (2012) pp. 1-31.

\* cited by examiner

METHODS FOR PREVENTING AND TREATING THROMBOTIC DISORDERS

CROSS REFERENCE TO RELATED APPLICATION

This application is a continuation-in-part of U.S. patent application Ser. No. 10/802,000, entitled "Compositions and Methods to Prevent Toxicity of Antiinflamatory Agents and Enhance their Efficacy", filed on Mar. 16, 2004, and which is a continuation-in-part of U.S. patent application Ser. No. 09/881,199, filed Jul. 27, 2000, now U.S. Pat. No. 6,432,991 and U.S. patent application Ser. No. 10/137,342 now U.S. Pat. No. 6,635,667, the contents of which are herein incorporated by reference.

FIELD OF INVENTION

This invention relates to thrombotic diseases. Specifically, the prevention and treatment of thrombotic disorders including, but not limited to, acute coronary syndrome, myocardial infarction, unstable angina, stroke, transient ischemic attack (TIA), deep vein thrombosis (DVT), pulmonary embolism (PE), thrombosis following angioplasty or stent placement, and peripheral vascular disease.

BACKGROUND OF THE INVENTION

Vascular disease, characterized as cardiovascular (CVD), cerebrovascular and peripheral vascular (PVD, also called peripheral arterial disease (PAD)), is the leading cause of death and disability in the Unites States, and is a rapidly emerging cause of death in the developing world. In the US alone, 2500 deaths per day are caused by CVD and the annual cost of the disease exceeds $400 billion (Rosmond, W., et al, Heart disease and stroke statistics-2007 update: a report from the American Heart Association Statistics Committee and Stroke Statistics Subcommittee, Circulation, Feb. 6, 2007; 115(5):e69-e171; Spinier S A, Pharmacotherapy, 2006; 26:209S-217S). Cerebrovascular disease includes Transient Ischemic attack (TIA) and stroke (brain attack). PVD or PAD is the presence of stenosis or occlusion in the aorta or arteries of the limbs, usually caused by atherosclerosis. PAD is prevalent after age 50 and is associated with significant increase in cardiovascular and cerebrovascular events (Sontheimer, D. L., Peripheral vascular disease: diagnosis and treatment, Am Fam Physician. Jun. 1, 2006; 73(11):1971-6). Approximately 240,000 TIAs, defined as a rapid disturbance of cerebral function due to cerebrovascular dysfunction lasting less than 24 hours, are diagnosed every year in the US and the numbers of undiagnosed TIAs are significantly higher (Johnson S. C., et al.; Ann Neurol. 2006, 60:301-313). The risk of a subsequent stroke after TIA is high, particularly in the first few days. So aggressive antiplatelet therapy is recommended to prevent further TIA or stroke.

Stroke, which includes ischemic (80% of strokes) and hemorrhagic, result from sudden onset of neurological deficit from interrupted blood supply to certain brain areas. Ischemic stroke results from embolic occlusion of large cerebral blood vessels or plaque buildup in the walls of blood vessels. High blood pressure and other factors can cause the plaque to rupture, triggering the platelets to aggregate and form a clot. Currently 700,000 Americans per year suffer a stroke and about 29% of these patients over 65 years of age die within 1 year. Worldwide, stroke is the third leading cause of death and severe disability in adults, with 20.5 million strokes and 5.5 million deaths (American Heart Association, Heart Disease and Stroke Statistics-2005 update).

Thrombosis, defined by local blood clotting, can occur in the arterial or the venous circulation. Platelet activation is a common factor in inflammatory diseases such as vascular disease (May A. E., et al., Atheroscier Thromb Vasc Biol. 2008; 28: s5-s10). Though enucleated, platelets can synthesize proteins by translational mechanisms, and a complex membranous system that allows them to store and rapidly release a variety of factors, such as monoamines, adhesion proteins, growth factors, chemokines, cytokines, and coagulation factors. Upon activation, platelets adhere to the endothelium and release adhesion factors, such as fibrogen.

Because thrombosis plays a major role in the pathogenesis of ischemic stroke, drugs that interfere with hemostasis and clot formation, such as anticoagulants and antiplatelet drugs are used for the management and prevention of stroke. Current treatment comprises thrombolytic therapy with tissue plasminogen activator (tPA), the only acute stroke treatment approved by the FDA in 1996 (Mitka, M., Rapid stroke treatment an elusive goal, JAMA, Apr. 9, 2008; 299(14):1653-4). Administration of tPA must be initiated within 3 hours of symptom onset, limiting practical use to a small proportion (less than 5%) of stroke victims, and is also associated with risk of intracerebral bleeding.

Current medical treatment for PVD includes administering anticoagulants to treat and prevent arterial or venous thrombosis, and reducing platelet aggregation by antiplatelet drugs such as aspirin and clopidogrel.

Because platelets have a role in the initiation and propagation of inflammation in their microenvironment, novel uses of antiplatelet drugs in the following conditions (infection, asthma and rhinitis, chronic obstructive pulmonary disease, cancer, rheumatoid arthritis, inflammatory bowel disease) are being investigated (Pitchford S. C.; Novel uses for anti-platelet agents as anti-inflammatory drugs, British J. Pharmacology, December 2007; 152(7): 987-1002).

Aspirin (Acetylsalicylic acid; ASA) irreversibly inhibits platelet cyclooxygenase 1, which catalyses the formation of thromboxane A2 (TXA2), a potent activator of platelets. Aspirin significantly reduces the risk of CVD (relative risk reduction of 25%) as well as reduces the risk of subsequent events (secondary prevention) in patients with previous history of CVD. But aspirin use is associated with risks such as stomach ulcers and bleeding. Moreover, the beneficial vascular effects are limited to lower doses, as high doses do not exhibit more effective vascular risk reduction and may blunt the antithrombic effect of low dose treatment (Patrono, C. & Rocca, B., Aspirin: Promise and resistance in the new millennium, Arterioscler. Throm. Vasc. Biol., 2008 March; 28(3): s25-32.). There have been several attempts to enhance the benefits of aspirin, using other antiplatelet drugs with different pharmacological actions on the platelet. However, use of drugs such as clopidogrel, prasugrel, ticlopidine, or dipyrimadole have so far not produced any significant improvements from treatment with aspirin alone, especially when one considers the high cost of these medications and the increased incidence of bleeding.

Dipyridamole (DP) is a phosphodiesterase inhibitor that increases the intracellular levels of cyclic AMP and cyclic GMP, and inhibits the uptake of adenosine, thereby reversibly inhibiting platelet aggregation and platelet-mediated thrombus formation.

Other anti-thrombotic drugs include ADP-receptor antagonists, αIIbβ-3-Intergrin inhibitors, and Protease-activated-receptor-1 (PAR1) inhibitors. ADP-receptor antagonists, like ticlopidine, clopidogrel and prasugrel, inhibit platelet activation by blocking ADP receptor $P_2Y_{12}$. Clopidogrel, in combination with aspirin is used for the prevention of acute coronary syndromes, secondary prevention of cardiovascular events, and stent thrombosis, whereas ticlopidine is not currently used due to serious side effects such as rash, neutropenia, and agranulocytosis. αIIbβ-3-intergrin inhibitors reduce platelet aggregation by blocking the binding of activated platelets to fibrinogen and other ligands. However, inhibitors like abiciximab, eptifibatide, and tirofiban are used only for short-term treatment of acute coronary syndromes as intravenous injections; oral formulations of these drugs are not used due to serious side effects.

Anticoagulant drugs reduce the activity of various proteases in the coagulation cascade. The major anticoagulant classes are vitamin K antagonists, heparins and inhibitors of factor Xa and thrombin. These drugs have serious side effects including bleeding. Antiplatelets drugs are used in acute thrombotic events and are also used prophylactically to reduce the incidence of arterial thrombosis in patients with CVD. The primary targets of antiplatelet therapy are molecules involved in platelet activation and aggregation. Another method for treatment for acute thrombotic events is the use of fibrinolytic agents (clot busters) like plasminogen activator and streptokinase. However this treatment has a short window of few hours to be successful. Recent studies have identified a number of novel platelet receptors and signaling mechanisms as targets for antiplatelet therapy.

The goal of secondary stroke prevention in patients who have suffered a stroke or transient ischemic attack (TIA) is to prevent recurrent cerebrovascular events. The rate of a recurrent stroke is estimated to be between 25-40% within 5 years, after the initial event. The strategy for secondary prevention includes risk factor modification, drug therapy, and surgery, when appropriate. The use of antiplatelet agents to treat or prevent recurrent TIA and stroke is a popular approach. There are numerous studies supporting the efficacy of aspirin, clopidogrel, and dipyridamole alone or in combination.

There is strong data to support the contention that long-term aspirin use reduces the risks of myocardial infarction, stroke, and vascular related deaths in patients with vascular disease. Up to 30% of patients on aspirin antithrombotic therapy have recurrent major vascular events each year, a phenomenon termed aspirin resistance. Patients who are resistant to aspirin are at a higher risk for cardiovascular morbidity long term than patients who respond to aspirin therapy (Krasopoulos, G. et al; Aspirin "resistance" and risk of cardiovascular morbidity: systematic review and meta-analysis, Jan. 26, 2008, Br Med J; 336(7637):195-8). Variable antiplatelet responses to other antithrombotic drugs, like clopidogrel, have also been reported by several studies. The mechanisms responsible for this decreased platelet response have not been clearly determined. But clopidogrel resistance is a marker for increased risk of recurrent vascular events (Campo, G. et al; Poor responsiveness to clopidogrel: drug-specific or class-effect mechanism? Evidence from a clopidogrel-to-ticlopidine crossover study; J Am Coll Cardiol, Sep. 18, 2007; 50(12):1132-7). Response to aspirin or clopidogrel may be modified by factors such as noncompliance, inadequate dose, poor absorption or metabolism, concomitant medications, and polymorphisms. Combination therapy with other antiplatelet agents is a therapeutic option in patients with aspirin or clopidogrel resistance. Duel antiplatelet therapies were first investigated using thienopyridines, drugs that block adenosine 5'-diphosphate-dependent activation of platelets mediated by ADP-$P2Y_{12}$ receptors. Duel therapy using aspirin and thienopyridines such as clopidogrel and ticlopidine has been actively investigated. However, drug safety profiles and antiplatelet efficacy question the use of aspirin-thienopyridine duel antiplatelet therapies (Bhatt D. L., et al.; Clopidogrel for High Atherothrombobitic Risk and Ischemic Stabilization, Management, and Avoidance (CHARISMA) Investigators, Clopidogrel and aspirin versus aspirin alone for the prevention of atherothrombotic events, N Engl J Med; 2006; 354, 1706-1717). New, third generation thienopyridines, such as prasugrel, ticagrelor, and cangrelor, are currently being investigated.

An ideal antiplatelet drug—one that will prevent thrombosis, without promoting bleeding—has yet to be found. A promising new approach is combination therapy, administering new agents with existing antiplatelet and anticoagulant drugs, which might prove more effective than using a single class of drug. Dual antiplatelet therapy with combinations of aspirin and clopidogrel or aspirin and dipyridamole has limited applications in thrombotic disorders. But these combinations do not necessarily improve clinical efficacy and are associated with a substantial increase in bleeding risk. These strategies are far from ideal, as most treatments have severe adverse side effects, including internal bleeding, and aspirin/clopidorel resistance.

Despite increased understanding of thrombogenesis and vascular function, therapeutic strategies to ameliorate the impact of vascular diseases are far from satisfactory. There is an urgent and unmet medical need to enhance the efficacy of currently available antiplatelet drugs in preventing and treating the overwhelming burden of the number one cause of death and disability worldwide, vascular disease.

SUMMARY OF INVENTION

The present invention is a combination therapy with MAO-B inhibitors and antiplatelet agents including, but not limited to aspirin, dipyridamole, clopidogrel, prasugrel, ticlopidine and αIIbβ-3-Intergrin inhibitors (abiciximab, tirofiban and aptifibatide).

Further evidence of inadequate platelet inhibition by aspirin is illustrated by recent studies of urinary 11-dehydro thromboxane $B_2$, a metabolite of thromboxane platelet activators. Urinary 11-dehydro thromboxane $B_2$ levels indicate aspirin regimes may have a limited effect on thromboxane levels (Eikelboom, J., et al; Incomplete inhibition of thromboxane biosynthesis by acetylsalicylic acid: determinants and effect on cardiovascular risk, 2008 Oct. 21, Circulation, 118 (17):1705-12). However, low dose aspirin-only treatment partially inhibits COX enzymes, allowing nucleated cells to regenerate COX-1 and synthesize prostaglandin $B_2$, thereby activating platelets. A combination treatment of clopidogrel and aspirin does not reduce thromboxane $B_2$ concentration or reduce cardiovascular risk, whereas non-steroidal anti-inflammatory drugs and statins did reduce thromboxane $B_2$ (Eikelboom, J., et al; Incomplete inhibition of thromboxane biosynthesis by acetylsalicylic acid: determinants and effect on cardiovascular risk, 2008 Oct. 21, Circulation, 118(17): 1705-12).

Further, concerns about the effectiveness of clopidogrel are raised by recent reports indicating that patients carrying certain gene variants respond less effectively to clopidogrel. Persistent high platelet reactivity and thrombotic events are observed in many patients on clopidogrel therapy due to inadequate inhibition of platelet $P2Y_{12}$ receptor. Clopidogrel is a prodrug that has to be converted to an active metabolite which irreversibly inhibits the platelet $P2Y_{12}$ receptor (Collet, J-P., et al; Cytochrome P450 2C19 polymorphism in young patients treated with clopidogrel after myocardial infarction: a cohort study, 2008 Dec. 23, Lancet). Intestinal absorption of the prodrug clopidogrel is limited by an intestinal efflux pump p-glycoprotein coded by the ABCB1 gene (Tabassome, S., et al; Genetic determinants of response to clopidogrel and cardiovascular events, 2008 Dec. 22, N. Engl. J. Med.). 85% of the prodrug is converted into inactive metabolites. Only 15% of the drug is converted to active metabolites in the liver by various cytochrome P450 isoforms (CY3A4, CYP3A5, CYP2C19). Polymorphisms in the genes coding for these proteins leads to loss-of-function of these enzymes and higher risk of cardiovascular events. In patients with a history of myocardial infarction and receiving acute or chronic clopidogrel therapy, those carrying CYP2C19 loss-of-function alleles experienced reduced clopidogrel responsiveness and a higher rate of subsequent cardiovascular events. Therefore, aspirin alone or in combination with clopidogrel is unable to provide adequate platelet inhibition.

Accordingly, a method is presented for preventing or treating thrombotic disease or inhibiting platelet reactivity, comprising administering a therapeutically effective amount of at least one monoamine oxidase B (MAO-B) inhibitor and an antithrombotic agent. In some embodiments, the MAO-B is 1-deprenyl, d-deprenyl, clorgyline, pargyline, nialamide, carboxamide, N-(2-aminoethyl)-5-chloropyridine-2-carboxamide, N-(2-Aminoethyl-4-chlorobenzamide), N-(2-aminoethyl-5-3-fluorophenyl thiazolecarboxamide), propargylamines, lazabemide, N-propargylamine compounds, N-methyl-propargylamine, N-methyl-N-(2-pentyl)-propargylamine, rasagiline, and derivatives thereof. The monoamine oxidase B inhibitor may be administered to a patient via oral, intravenous, intra-arterial, intra-articular, intra-cerebral, subcutaneous, transcutaneous, intraperitoneal, intraspinal, intrarectal, transcutaneous, intramuscular, or intranasal routes. In some embodiments, a patient is administered a dose of 1-deprenyl from between about 0.1 mg to 500 mg per day.

L-deprenyl has been found to act through NO-mediated and NO-independent effects on platelets, and is useful as an anti-platelet agent. Nitric oxide has been shown to inhibit platelet aggregation (Radomski, M. W., et al; Nitric oxide in platelets, Methods Enzymol. 1996; 269:88-107). While the mechanism of NO inhibition is not fully understood, NO is believed to target intracellular cytosolic guanylate cyclase (cGMP), and it is the elevated cGMP levels that inhibit platelet activation (Schmidt, et al., The nitric oxide and cGMP signal transduction system: regulation and mechanism of action; Biochem Biophys Acta, Aug. 18, 1993; 1178(2):153-75). Additionally, NO has been shown to inhibit mitochondrial respiration and low levels of NO selectively inhibit cytochrome oxidase (cytochrome aa3, complex IV) and act as an antagonist to intracellular oxygen (Brown, 2001). Reports also indicate NO can inhibit tricarboxylic acid cycle enzymes and mitochondrial energy production, thereby preventing platelet secretion and affecting aggregation (Tomasiak, M., et al., Nitric Oxide and platelet energy metabolism, *Acta Biochemica Polonica*, 51:789-804, 2004).

The method also provides for administration of at least one antithrombotic agent, which, without limitation, may be an antiplatelet drug or antithrombolytic drug. In some embodiments, the patient is administered tissue plasminogen activator. Alternatively, the patient may be administered, without limitation, a cyclooxygenase inhibitors, such as aspirin, salicylic acid, indomethacin, and trifusal, ADP receptor antagonists, such as ticlopidine, clopidogrel, clopidogrel bisulfate, and prasugrel, Dipyridamole, αIIbβ3-Intergrin inhibitors, such as abiciximab, tirofiban and eptifibatide, or Protease-activated-receptor-1 (PAR1) inhibitors.

Also disclosed is a method to enhance action of antithrombotic drug, comprising administering an effective amount of a plurality of compounds to a patient, which comprises an effective dose of an MAO inhibitor and an effective does of at least one cardiovascular drug. In some embodiments of the method, the cardiovascular drugs may be statins, lipid lowering drugs, HDL elevating drugs, antihypertensives, vasodilators, antiplatelet drugs, cyclooxygenase inhibitors, such as aspirin, salicylic acid, and trifusal, ADP receptor antagonists, such as ticlopidine, clopidogrel, and prasugrel, dipyridamole, αIIbβ3-Intergrin inhibitors, such as abiciximab, tirofiban and aptifibatide, and protease-activated-receptor-1 inhibitors, and antithrombolytic drugs, such as tissue plasminogen activator. The antiplatelet drug is a combination of aspirin and at least one compound in some embodiments. The combination may include clopidogrel, prasugrel, and dipyridamole.

The monoamine oxidase inhibitor used in the present methods may be administered via oral, intravenous, intra-arterial, intra-articular, intra-cerebral, subcutaneous, transcutaneous, intraperitoneal, intraspinal, intrarectal, transcutaneous, intramuscular, or intranasal routes.

A method is also presented for preventing, treating or reversing a disease, comprising administering a therapeutically effective amount of at least one monoamine oxidase B inhibitor and an antithrombotic agent; wherein the disease selected from the group consisting of cardiovascular disease, cerebrovascular disease, deep vein thrombosis, pulmonary embolism, venous thromboembolism, disseminated intravascular coagulation, peripheral vascular disease, peripheral arterial disease, thrombosis, platelet activation platelet aggregation, ischemia, reperfusion injury, and vascular disease. In some embodiments, the monoamine oxidase B inhibitor may be 1-deprenyl, d-deprenyl, clorgyline, pargyline, nialamide, carboxamide, N-(2-aminoethyl)-5-chloropyridine-2-carboxamide, N-(2-Aminoethyl-4-chlorobenzamide), N-(2-aminoethyl-5-3-fluorophenyl thiazolecarboxamide), propargylamines, N-propargylamine compounds, N-methyl-propargylamine, N-methyl-N-(2-pentyl)-propargylamine, rasagiline, and derivatives thereof. In some embodiments, the antithrombotic agent is an antiplatelet drug, such as cyclooxygenase inhibitors, ADP receptor antagonists, dipyridamole, αIIbβ3-Intergrin inhibitors, and Protease-activated-receptor-1 (PAR1) inhibitors, or antithrombolytic drug, such as tissue plasminogen activator. Without limiting the invention, the cyclooxygenase inhibitor is aspirin, salicylic acid, or trifusal. The ADP receptor antagonists may be, without limitation, ticlopidine, clopidogrel, and prasugrel. In some embodiments of the method where αIIbβ3-Intergrin inhibitors are employed, the αIIbβ3-Intergrin inhibitors may be abiciximab, tirofiban and eptifibatide.

The methods disclosed herein are useful in treating, without limitation, cardiovascular diseases such as acute coronary syndrome, myocardial infarction, and angina or cerebrovascular disease such as TIA, stroke, and vasospasm. The method further may prevent or reduce antiplatelet drug resistance, antiplatelet drug tolerance, antiplatelet drug side effects, platelet-leukocyte interaction, platelet-endothelial interaction, vascular dysfunction, cardiovascular risk associated with nonsteroidal anti-inflammatory drugs. Further, the monoamine oxidase inhibitor may be administered by oral, intravenous, intra-arterial, intra-articular, intra-cerebral, subcutaneous, transcutaneous, intraperitoneal, intraspinal, intrarectal, transcutaneous, intramuscular, or intranasal routes.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
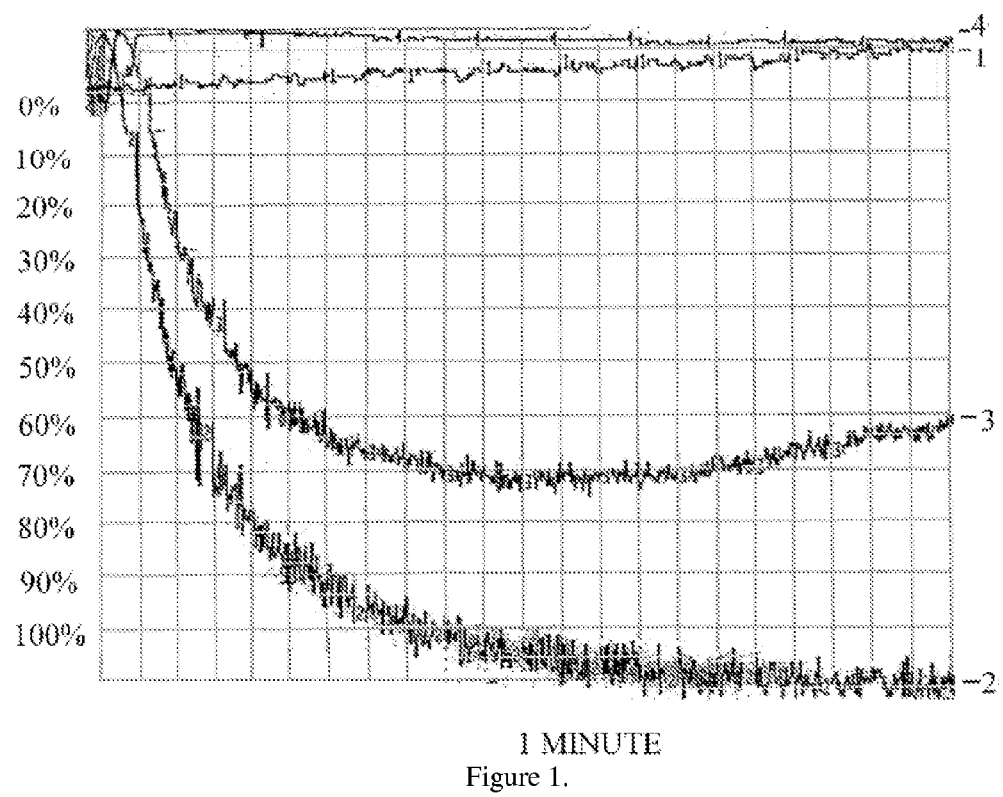
FIG. 1 is a graph showing the effect of 1-deprenyl on human platelet aggregation induced by ADP. The experimental groups are as follows: group 1 are control platelet cells treated with no ADP; group 2 are control cells treated with ADP only; group 3 are cells preincubated for 15 minutes with 50 µM 1-deprenyl, followed by ADP treatment; and group 4 are cells preincubated for 15 minutes with 100 µM 1-deprenyl, followed by ADP treatment.

"Patient" is used to describe an animal, preferably a human, to whom treatment is administered, including prophylactic treatment with the compositions of the present invention.

The "therapeutically effective amount" for purposes herein is thus determined by such considerations as are known in the art. A therapeutically effective amount of the compounds, including without limitation, antiplatelet drugs, antithrombolytic drugs, cardiovascular drugs, MAO inhibitors, or any combination thereof is that amount necessary to provide a therapeutically effective result in vivo. The amount of the compounds, including without limitation, antiplatelet drugs, antithrombolytic drugs, cardiovascular drugs, MAO inhibitors, or any combination thereof must be effective to achieve a response, including but not limited to total prevention of (e.g., protection against) and to improved survival rate or more rapid recovery, or improvement or elimination of symptoms associated with thrombotic events, stroke, cardiovascular disease, and neural damage, or other indicators as are selected as appropriate measures by those skilled in the art. In accordance with the present invention, a suitable single dose size is a dose that is capable of preventing or alleviating (reducing or eliminating) a symptom in a patient when administered one or more times over a suitable time period. The "therapeutically effective amount" of a compound of the present invention will depend on the route of administration, type of patient being treated, and the physical characteristics of the patient. These factors and their relationship to dose are well known to one of skill in the medicinal art.

"Administration" or "administering" is used to describe the process in which compounds of the present invention, alone or in combination with other compounds, are delivered to a patient. The composition may be administered in various ways including oral, parenteral (referring to intravenous and intraarterial and other appropriate parenteral routes), intratheceally, intramuscularly, subcutaneously, colonically, rectally, and nasally, transcutaneuosly, among others. Each of these conditions may be readily treated using other administration routes of compounds of the present invention to treat a disease or condition. The dosing of compounds and compositions of the present invention to obtain a therapeutic or prophylactic effect is determined by the circumstances of the patient, as known in the art. The dosing of a patient herein may be accomplished through individual or unit doses of the compounds or compositions herein or by a combined or pre-packaged or pre-formulated dose of a compounds or compositions.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjutants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W [1995] Easton Pa., Mack Publishing Company, 19$^{th}$ ed.) describes formulations that can be used in connection with the subject invention.

MAO-A or MAO-B inhibitors have been found to act in modes unrelated to actions as a selective MAO-A or MAO-B inhibitor. For example, L-deprenyl exerts effects on both cerebral and peripheral vasculature, some of which are mediated by nitric oxide (NO) and others of which are NO-independent. More particularly, MAO-B inhibitors such as L-deprenyl have been found to stimulate NO production rapidly and stereospecifically when administered in vitro or in vivo to peripheral or cerebral blood vessels. They also have been found to blunt the vasoconstriction caused by a number of vasoconstrictors.

L-deprenyl at low doses (≤10 µM) causes rapid NO-mediated endothelium-dependent vasodilation. At higher doses L-deprenyl produces a slow progressive NO- and endothelium-independent direct relaxation of vascular smooth muscle. The NO-mediated, endothelial-dependent effects of L-deprenyl and other MAO-A or MAO-B inhibitors on the cerebral and peripheral vasculature makes them useful in treating a variety of disorders, including essential, renovascular and pulmonary hypertension, glaucoma (by reduction of intraocular pressure), macular degeneration, and erectile impotence all of which result from a significant reduction of endothelium-dependent relaxation. MAO-A or MAO-B inhibitors such as L-deprenyl also have been discovered to exert a potent relaxant effect on non-vascular smooth muscle, which is mediated both by guanylate cyclase and cyclic GMP-independent mechanisms. L-deprenyl also exerts a relaxant effect on non-vascular smooth muscle, mediated by both guanylate cyclase and cyclic GMP-independent pathways.

MAO inhibitors also are useful in cases of myocardial infarction and cerebrovascular stroke, which result from an alteration of endothelial function. The endothelium-independent direct relaxation of vascular smooth muscle by MAO-B inhibitors such as L-deprenyl can be a useful adjunct in treatment of these disorders. MAO-B inhibitors, such as 1-deprenyl, act in NO-mediated and NO-independent ways on platelets and inflammatory cells, such as mast cells, macrophages, and glial cells. Most notable in this context are their use as anti-platelet agents or as anti-inflammatory agents. Examples of treatable disorders include thrombosis, stroke and other cerebrovascular diseases, peripheral arterial disease, and peripheral vascular disease. Thus, MAO-B inhibitors such as 1-deprenyl can be used to affect both NO-mediated and NO-independent actions on the cerebral and peripheral vasculature, on non-vascular smooth muscle, and on a diverse group of other cells, including platelets. Activity has been observed for a wide variety of MAO-B inhibitors, including L-deprenyl, clorgyline, pargyline, RO-16-6491 (N-(2-aminoethyl)4-chlorobenzamide hydrochloride), and RO-41-1049 (N-(2-aminoethyl)-5-(3-fluorophenyl)-4-thiazolecarboxamide hydro-chloride). Each of these compounds has been shown to have the ability to inhibit contraction, to dilate blood vessels, to inhibit β-amyloid and to stimulate NO production. Derivatives of these compounds may be used, as well as other MAO-B inhibitors and derivatives thereof. Exemplary of compounds that are structurally related to L-deprenyl are N-propargylamine compounds, N-methyl-propargylamine and N-methyl-N-(2-pentyl)-propargylamine can be used in place of L-deprenyl.

MAO-B inhibitors have been found to possess anti-platelet and platelet anti-aggregation qualities. The ability to inhibit platelet aggregation and thrombus formation occurs through novel mechanisms unique and independent of aspirin. Surprisingly, MAO-B inhibitors also reverse thrombus formation. Administration of MAO-B inhibitors has also been shown to effectively treat patients with anti-platelet drug resistance, including without limitation aspirin resistance.

It is postulated that the cytoprotective effect of L-deprenyl and other MAO-A or MAO-B inhibitors is mediated by increased NO production, but it may be due in part to oxygen free radical scavenging by the compounds. MAO-B inhibitors, such as 1-deprenyl, also act as antioxidants. It was recently found that antioxidants are useful in modulating platelet activation (Freedman, J; Oxidative stress and platelets, Arteriosclerosis, Thrombosis, and Vascular Biology. 2008; 28: s11). Antioxidant supplements and compounds have also been shown to preserve NO activity, further reducing coronary risk. L-Deprenyl is a particularly potent stimulant of NO production, and concentrations as low as 1 µM have a stimulatory effect on NO production. Alternatively, the oxidization of low density lipoprotein (LDL), which has been shown to be atherogenic and promote platelet aggregation, is inhibited by 1-deprenyl.

L-Deprenyl and other MAO-B inhibitors can be administered orally in capsule form. The present invention provides a method of treating thrombotic diseases using a combination therapy with deprenyl (or propargylamine compounds) and antiplatelet agents including, but not limited to aspirin, dipyridamole, clopidogrel, prasugrel, ticlopidine and αIIbβ3-Intergrin inhibitors (abiciximab, tirofiban and aptifibatide). For example, a recommended daily regimen for administration of antiplatelet drugs in accordance with the present invention is aspirin 25 mg to 1200 mg bid, salicylic acid at 1 mg to 100 mg, trifusal at 100 mg to 900 mg, ticlopidine 50 mg to 500 mg bid, clopidogrel 75 mg to 600 mg qid, prasugrel 1 mg to 1000 mg qid, dipyridamole 50-400 mg qid, anagrelide 0.5 mg-5 mg qid, eptibatide 2 µg to 180 µg per kg, abiciximab 0.25 mg per kg to 20 mg per kg or 1 mg to 20 mg, tirofiban 0.1 microgram per kg to 25 microgram per kg or 25 µg/ml to 250 µg/ml, coumadin at 0.25 mg to 10 mg, tissue plasminogen activator (tPA) at 0.1 mg to 0.9 mg per kg, aspirin 25-50 mg and extended release dipyridamole 200-400 mg combination, aspirin 75 mg and clopidogrel 75-300 mg combination. These amounts can be adjusted depending on the physical condition of the patient and the severity of the disease.

The following examples illustrate various actions of L-deprenyl according to the present invention, but do not limit the scope of the invention in any way. Further aspects and variations of the invention, based on the disclosure above and the following examples, will be apparent to the person of ordinary skill in the art.

Methods

Platelet Aggregation Studies

Two 4.5 ml samples whole blood were collected into tubes containing 3.8% sodium citrate after various treatments and at different times as indicated in the examples. 500 microliter of whole blood was diluted with equal volume of 0.9% sodium chloride and prewarmed at 37° C. for 5 minutes. For optical studies, platelet rich plasma blood was mixed gently and immediately centrifuged at 180 g for 10 min to obtain platelet-rich plasma (PRP). Platelet poor plasma (PPP) was obtained by centrifugation at 1800 g for 15 minutes at room temperature. The platelet concentration in the PRP was adjusted to approximately $250 \times 10^9$ cells/l using PPP. Readings were taken at 37° C. at a stirring speed of 1200 rpm.

The platelet aggregation studies were performed by electrical impedance or the turbidometric methods according to Born's method (Born, G. V.; Aggregation of blood platelets by adenosine diphosphate and its reversal, Nature; 1962; 194:927-929) for whole blood (Chrono-Log aggregometer) and platelet rich plasma using a platelet aggregation profiler (PAP-4, Bio Data Corporation, Horsham, Pa.). Aggregation agonists were used at a final concentration of $2.0 \times 10^{-5}$ M for ADP, 0.19 mg/ml for collagen, 500 µg/ml for arachidonic acid, and $1 \times 10^{-4}$ M for epinephrine. During the study, optical density was continuously recorded. The 0% and 100% aggregation levels were set with PRP and PPP, respectively. The maximal percentage of platelet aggregation was calculated as the light transmission between platelet-rich and platelet-poor plasma (100%). When a stable baseline was obtained with 450 µl of PRP, 50 µl of one of the aggregation-inducing agents was added. The maximum height and slope of the aggregation curves were determined. After the electrode was immersed in the sample, platelet aggregation to various agonists (collagen, ADP, arachidonic acid or epinephrine) was measured in ohms of impedance. The lag phase was defined as the delay time occurring between the addition of collagen and the beginning of the aggregation curve.

In Vivo Thrombosis Studies

The effect of treatment on infarct volume was determined as described previously (Puig, N., et al.; Serum amino acid levels after permanent middle cerebral artery occlusion in the rat, Cerebrovascular Diseases, 2000; 10:449-454). Adult male rats weighing 200-250 g were anesthetized. Focal cerebral ischemia was induced by ligature of the left common carotid artery and occlusion of the ipsilateral distal middle cerebral artery (MCAO). Aspirin (30 mg/kg) and 1-deprenyl (10 mg/kg) were injected intrapertoneally 2 hours prior to MCAO. Rats subjected to sham MCAO operation served as control. To determine infarct volume, the brains were removed 48 hours after MCAO and a series of coronal brain slices were obtained and stained with 1% 2,3,5-triphenyl-tetrazolium chloride in 0.1M phosphate buffer. The infarct volume was determined by adding the infarct volumes, which were unstained by the dye. Mean results are depicted, SEM<0.1.

Platelet aggregation has been shown inducible by G-protein-coupled receptors on platelets that respond to adenosine 5'-diphosphate (ADP), collagen, arachidonic acid, among other agonists (Ohlmann, P., et al., ADP induces partial platelet aggregation without shape change and potentiates collagen-induced aggregation in the absence of Gαq, Blood. 2000; 96:2134-2139). ADP is a unique agonist, in that it induces platelet aggregation through the P2Y1 and another P2 receptor, and also potentiates aggregation from other stimuli through the P2cyc receptor. Collagen and arachidonic acid stimulate aggregation through GPIa/IIa respectively (Coller, B., et al., Blood, 74:182-192, 2008). ADP, collagen, and arachidonic acid are well known in the art as strong aggregation inducers.

EXAMPLE 1

Effect of 1-Deprenyl on Human Platelets

L-deprenyl was evaluated to determine its ability to prevent aggregation. L-deprenyl was added to two samples of human platelet rich plasma at 50 µM and 100 µM for 15 minutes. After transferring the samples into aggregometer vials, ADP was added at a final concentration of $2 \times 10^{-5}$ M, to the aliquots to induce aggregation and measurements taken. As seen in FIG. 1, introducing ADP to the plasma resulted in rapid aggregation. Within 5 minutes of ADP alone, platelet aggregation reached 80%. Preincubation with 50 µM 1-deprenyl provided a partial protection, slowing down the aggregation rate, compared to ADP alone, and lessening the maximum aggregation percentage to approximately 70%. However, preincubation in 100 µM 1-deprenyl provided complete protection from ADP-induced aggregation, seen in FIG. 1.

Figure 2:
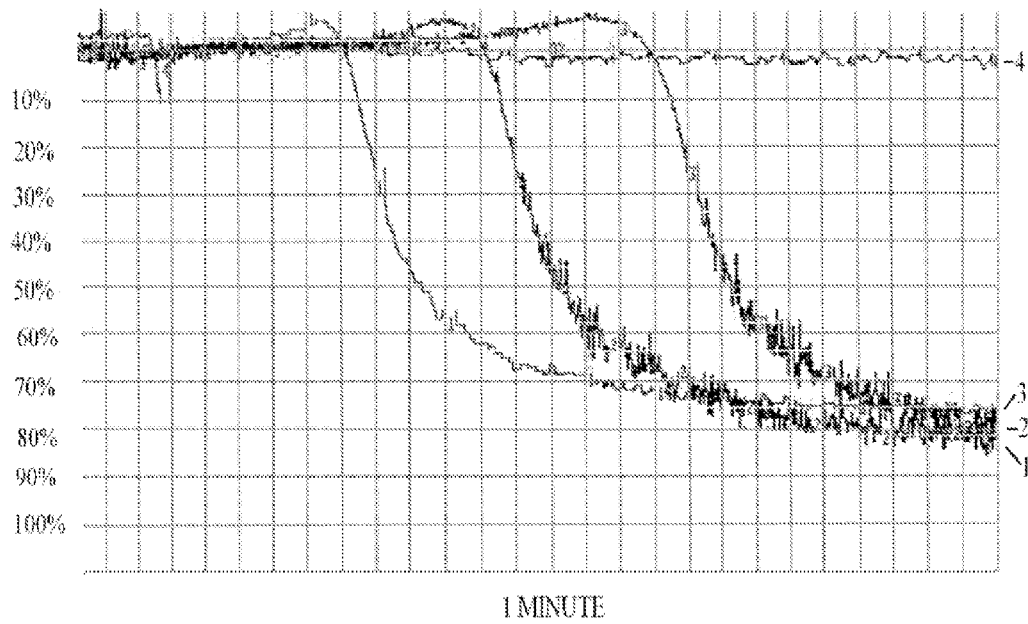
FIG. 2 is a graph showing the effect of 1-deprenyl on human platelet aggregation induced by collagen. The experimental groups are as follows: group 1 are control cells treated with collagen only; group 2 are cells preincubated for 15 minutes with 25 µM 1-deprenyl followed by collagen treatment; group 3 are cells preincubated for 15 minutes with 50 µM 1-deprenyl followed by collagen treatment; and group 4 are cells preincubated for 15 minutes with 100 µM 1-deprenyl followed by collagen treatment.
Figure 3:
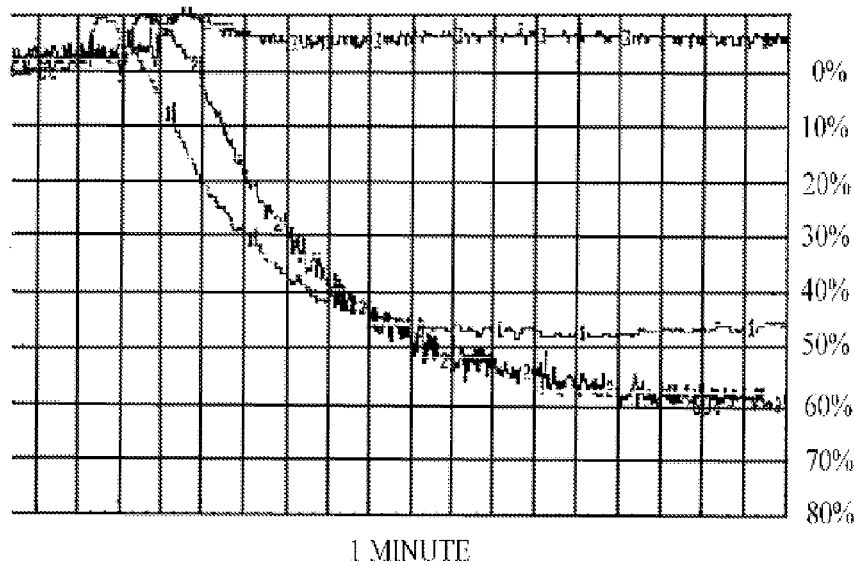
FIG. 3 is a graph showing the effect of 1-deprenyl on human platelet aggregation induced by arachidonic acid. The experimental groups are as follows: group 1 are control cells treated arachidonic acid only; group 2 are control cells treated arachidonic acid only; and group 3 are cells preincubated for 15 minutes with 100 µM 1-deprenyl, followed by arachidonic acid treatment.

L-deprenyl's inhibitory effects were further examined with collagen and arachidonic acid. L-deprenyl was added to aliquots of plasma at concentrations of 25 µM, 50 µM, and 100 µM and incubated for 15 minutes, followed by addition of collagen or arachidonic acid. As seen in FIG. 2, lower concentrations of 1-deprenyl, at 25 µM and 50 µM, did not reduce overall aggregation, but did delay onset of collagen-induced aggregation. However, the 100 µM 1-deprenyl treatment provided almost complete protection from aggregation, with only trace levels of aggregation detectable. Likewise, plasma treated with 100 µM 1-deprenyl prevented aggregation in arachidonic acid induced samples, seen in FIG. 3. Taken together, these results indicate 1-deprenyl inhibits platelet aggregation in a dose dependent manner. Further, the platelet aggregation-inhibitory effects of 1-deprenyl were observed in both male and female humans, in both whole blood and platelet rich plasma.

Figure 4:
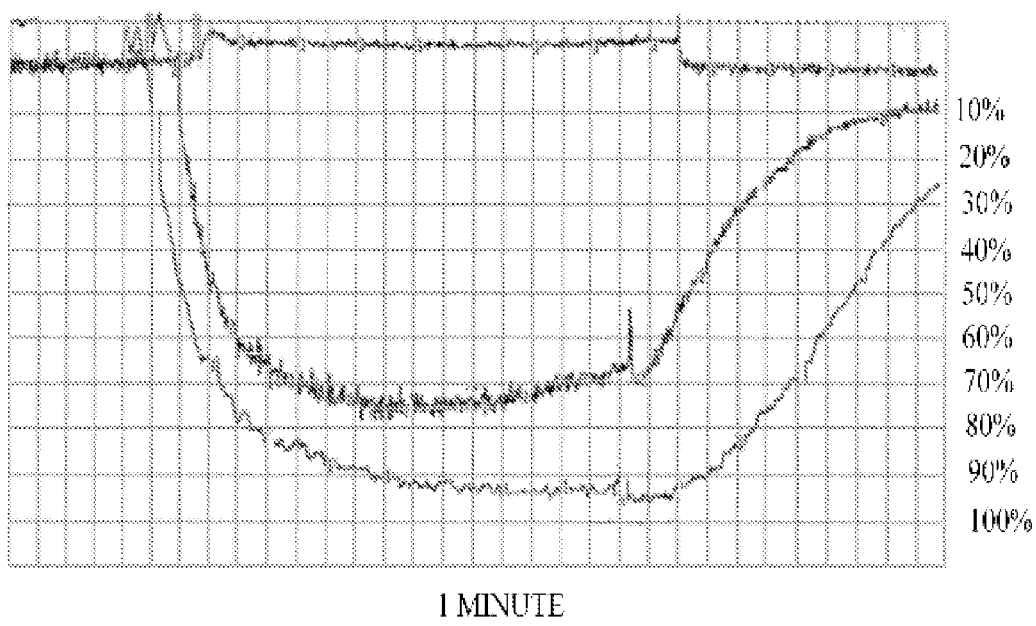
FIG. 4 is a graph showing the effect of 1-deprenyl on reversing human platelet aggregation induced by ADP. The experimental groups are as follows: group 1 are control cells treated with ADP only; group 2 are cells were treated with ADP and administered 100 µM 1-deprenyl following aggregation, as indicated by the arrow; and group 3 are control cells not treated with ADP.

The effect of 1-deprenyl acts through novel pathways compared to aspirin, allowing anti-thrombic treatment of aspirin-resistant subjects. An aspirin-resistant human subject was identified, treated with daily doses of 81 mg aspirin with no evident anti-thrombic effect. Platelet rich plasma was collected and samples preincubated for 15 minutes with 100 µM 1-deprenyl. Addition of collagen to untreated samples resulted in a sharp increase in platelet aggregation. The administration of 1-deprenyl prevented aggregation, and prevented all but negligible platelet aggregation, as seen in FIG. 4. The effects observed in aspirin-resistant individual indicate 1-deprenyl functions through different pathways than aspirin.

Platelet lactate dehydrogenase activity was then measured to determine platelet damage. Platelet samples were exposed to 1-deprenyl and LDH activity measured within an LDH assay kit (Cayman Chemical Co., Ann Arbor, Mich.). Released LDH levels were compared with total LDH activity in platelets dissolved in 0.1% Triton X-100, with no increase in extracellular LDH levels observed in the presence of 1-deprenyl (data not shown). This indicates 1-deprenyl has no cytotoxic effect on human platelets, and did not alter the cellular integrity of the platelets.

EXAMPLE 2

Reversal of Platelet Aggregation by 1-Deprenyl

Figure 5:
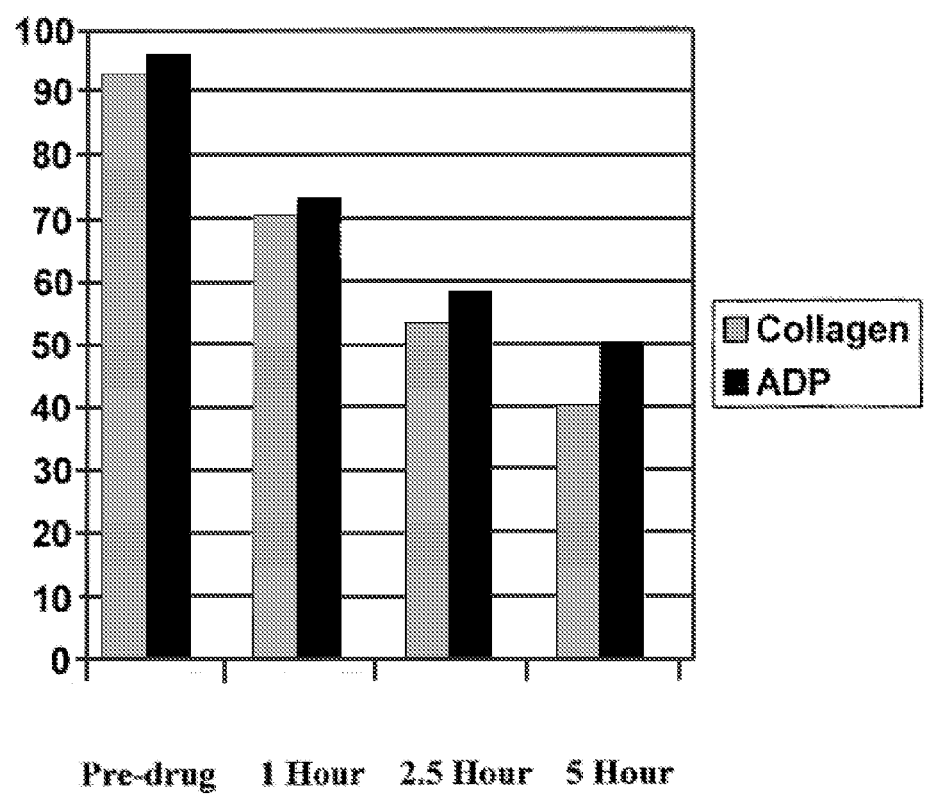
FIG. 5 is a bar graph showing the effect of 1-deprenyl delivered via a skin patch on human platelet aggregation induced by ADP or collagen. Blood was withdrawn at indicated times and aggregation studies conducted. At 24 hours after skin patch administration of 1-deprenyl, there was a 10% inhibition of aggregation compared with control (data not shown).

Plasma blood was separated into three experimental groups. One group (number 2) was preincubated for 15 minutes with 100 µM 1-deprenyl. ADP was then administered to experimental groups 1 and 2, seen in FIG. 5. During measurements, an additional 100 µM 1-deprenyl was added to groups 1 and 2 as indicated by the arrow. As before, preincubation of 1-deprenyl to platelets delayed aggregation onset and reduced the maximum amount of aggregation. Moreover, the addition of 1-deprenyl after platelet aggregation caused both the pre-incubated sample (group 2) and non-preincubated sample (group 1) aggregation to recede immediately. Administration of 1-deprenyl to both sample decreased aggregation levels to levels similar to non-ADP treated platelets (group 3), seen in FIG. 5.

EXAMPLE 3

Inhibition of Platelet Aggregation by 1-Deprenyl by Skin Delivery

Figure 6:
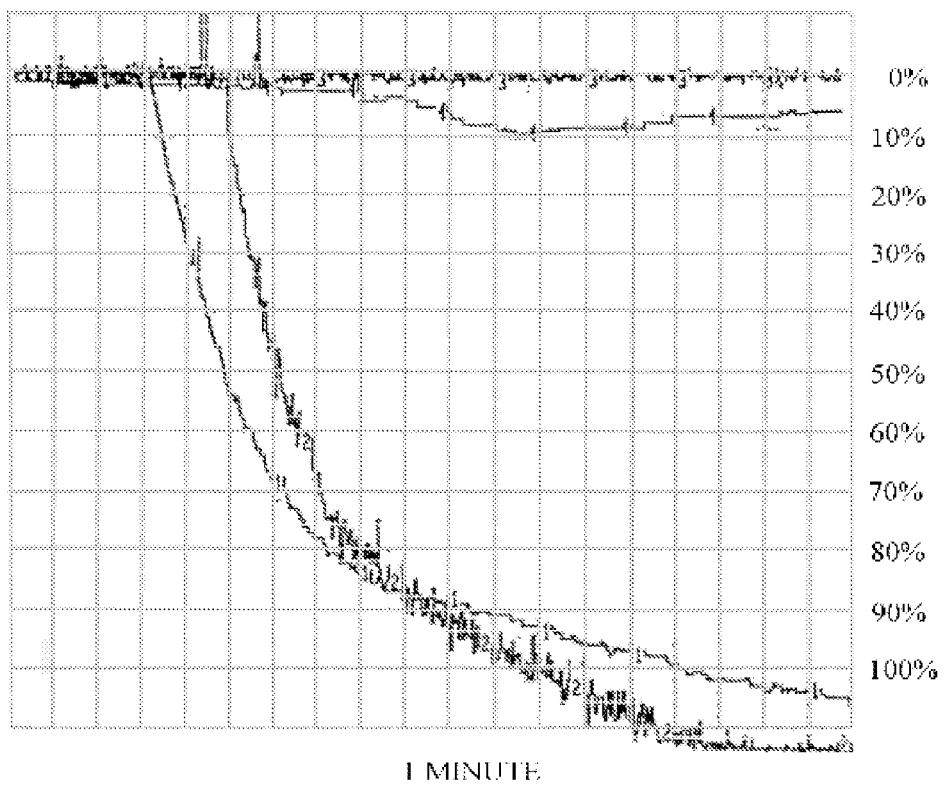
FIG. 6 is a graph showing the effect of 1-deprenyl on human platelet aggregation within an aspirin resistant patient. The patient administered 81 mg of aspirin daily with no anti-thrombotic effects. The experimental groups are as follows: group 1 are control cells treated with collagen only; group 2 are control cells treated with collagen only; group 3 are cells were preincubated with 100 µM 1-deprenyl, followed by treatment with collagen; group 4 are cells were preincubated with 100 µM 1-deprenyl, followed by treatment with collagen.

L-deprenyl was administered transcutaneously through skin patches (12 mg, EMSAM) for 24 hours. Blood was drawn prior to administration of the skin patch, and at 1 hour, 2.5 hours, and 5 hours after administration. The samples were subsequently treated with collagen or ADP and aggregation levels determined, as seen in FIG. 6. L-deprenyl inhibited platelet aggregation caused by both agonists, with a more pronounced effect on collagen than ADP. By 24 hours after administration, 1-deprenyl reduced aggregation by 10% of the control value.

EXAMPLE 4

Enhancement of Aspirin Action by 1-Deprenyl

Figure 7:
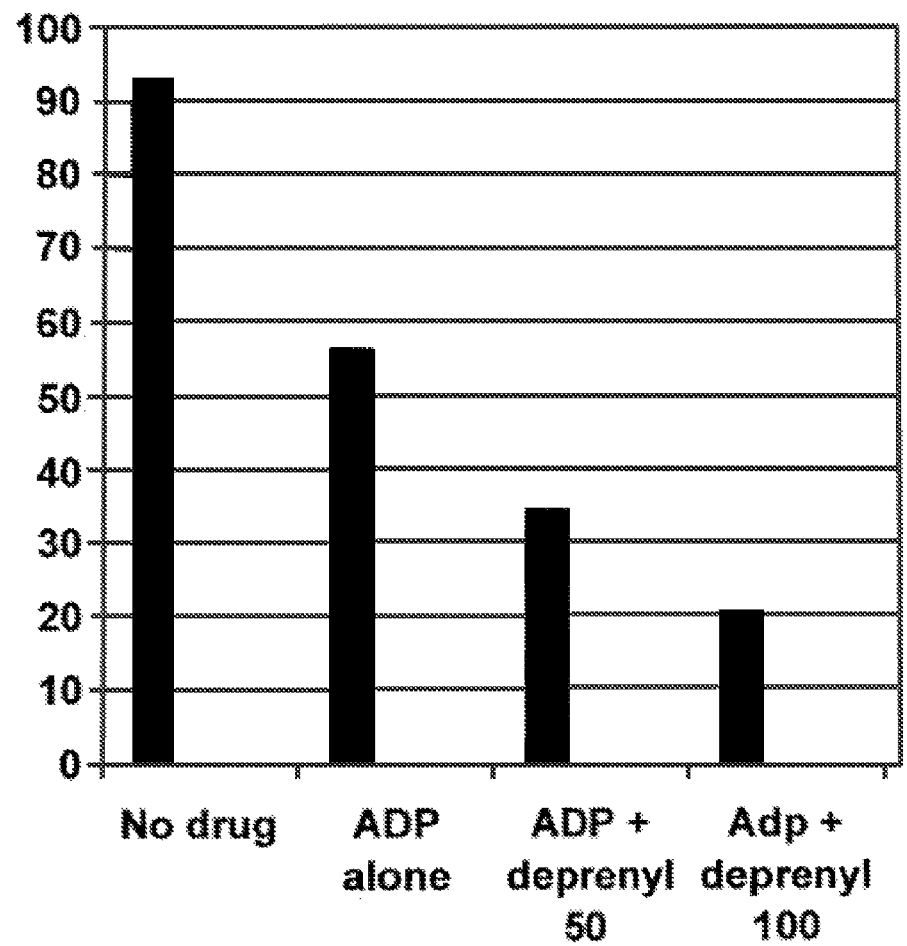
FIG. 7 is a bar graph showing the effect of 1-deprenyl on human platelet aggregation after short-term administration of aspirin and clopidogrel. The patient was administered 81 mg aspirin and 75 mg clopidogrel daily for 3 days. Blood was withdrawn prior to any treatment, after three days of treatment with aspirin and clopidogrel. Blood samples were separated into four groups; one without further treatment, one without anti-thrombotic drugs; one incubated with 50 µM 1-deprenyl for 15 minutes; and one incubated with 100 µM 1-deprenyl for 15 minutes. Three samples were then treated with ADP, as indicated, and aggregation studies conducted.

A human subject was orally administered a combination treatment of 81 mg aspirin and 75 mg clopidogrel for 3 days. Blood samples were taken before any treatment and after the 3-day aspirin-clopidogrel treatment. Blood taken after treatment was then separated and administered either no 1-deprenyl, or 50 µM or 100 µM 1-deprenyl and aggregation tests were performed using ADP. Baseline platelet aggregation, before any drug treatment, exhibits a 95% aggregation rate, as seen in FIG. 7. Combination treatment with aspirin and clopidogrel reduced the rate to approximately 57%, whereas the addition of 50 µM or 100 µM 1-deprenyl reduced aggregation to approximately 35% and 22%, respectively. L-deprenyl thus acts in concert with other anti-thrombic drugs.

Figure 8:
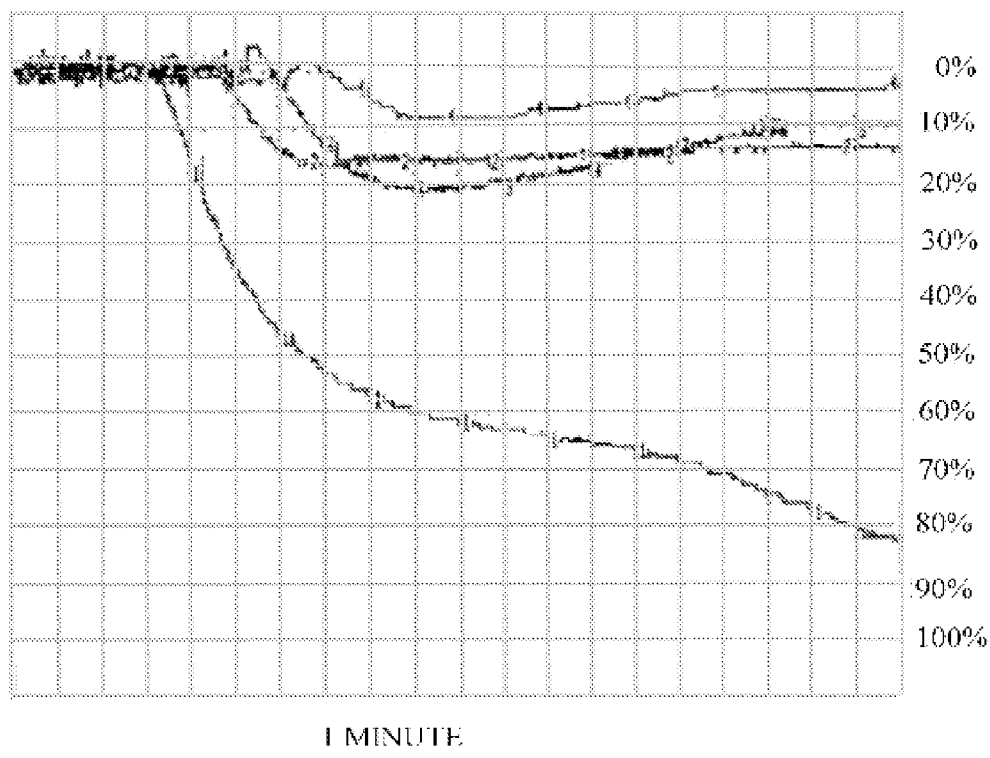
FIG. 8 is a graph showing the effect of 1-deprenyl on human platelet aggregation after long-term term administration of aspirin and clopidogrel. The patient was administered 81 mg of aspirin and 75 mg clopidogrel daily for 3 months. Blood was withdrawn and separated into four groups; two groups without further anti-thrombotic drugs; and two incubated with 100 µM 1-deprenyl for 15 minutes. Group 1 is control cells treated with collagen without anti-thrombotic drugs. Group 2 are control cells treated with ADP without anti-thrombotic drugs. Group 3 cells were preincubated with 1-deprenyl followed by treatment with collagen. Group 3 cells were preincubated with 1-deprenyl followed by treatment with ADP. Aggregation studies were then conducted on the samples.

L-deprenyl was also found to be efficacious in enhancing long-term aspirin and clopidogrel treatments. A human subject with a history of cardiovascular disease was identified. The subject receives a drug regimen of 81 mg aspirin and 75 mg clopidogrel (Plavix™). Blood samples were obtained and separated into 4 groups. Two groups (groups 3 and 4) received 100 µM 1-deprenyl preincubation treatments for 15 minutes as before. The samples were then given collagen (groups 1 and 4) or ADP (groups 2 and 3), and platelet aggregation observed. The aspirin-clopidogrel long-term treatment reached a maximum aggregation rate of about 85% and failed to appreciably effect aggregation, as seen in FIG. 8. Addition of 1-deprenyl dramatically reduced aggregation to near-negligible levels and delayed onset of aggregation. Conversely, the long-term aspirin-clopidogrel treatment did appear to affect ADP-induced aggregation, with a maximum rate of about 15%. Addition of 1-deprenyl slightly delayed aggregation onset. Further, while 1-deprenyl did not reduce maximum aggregation levels, the levels peaked around 20% and then stabilized to about 10% aggregation, providing a slight reduction in overall platelet aggregation.

EXAMPLE 5

Inhibition of Platelet Aggregation by Other MAO-B Inhibitors

Figure 9:
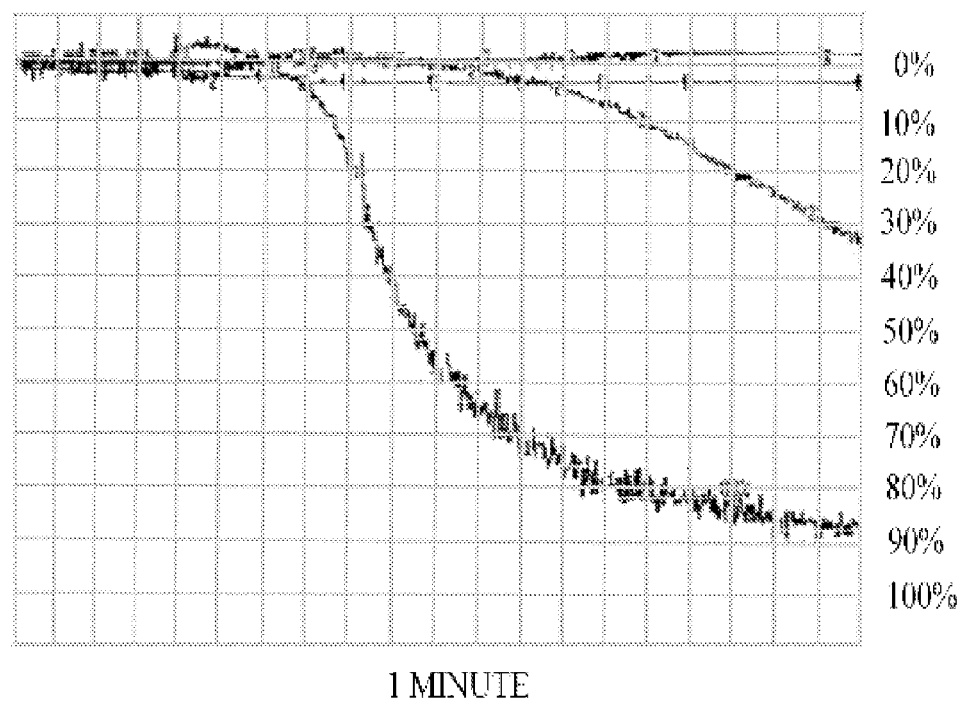
FIG. 9 is a graph showing the effect of rasagiline on human platelet aggregation induced by collagen. The experimental groups are as follows: group 1 are control cells treated collagen only; group 2 are cells preincubated for 15 minutes with 50 µM rasagiline, followed by collagen treatment; group 3 are cells preincubated for 15 minutes with 100 µM rasagiline, followed by collagen treatment; and group 4 are control cells treated with no collagen.

Other MAO inhibitors were tested for 1-deprenyl's inhibitory effects to determine whether this effect is specific to 1-deprenyl. Blood samples were preincubated in 50 µM or 100 µM rasagiline, a MAO-B inhibitor, for 15 minutes and aggregation stimulated using collagen. Baseline platelet aggregation peaked around 89%. Rasagiline treatment reduced peak aggregation to 35% for 50 µM rasagiline and negligible levels for 100 µM rasagiline, seen in FIG. 9. Aggregation onset was also delayed by treatment with rasagiline. Moreover, treatment with 100 µM rasagiline resulted in a 69% inhibition in ADP-induced platelet aggregation (data not shown).

EXAMPLE 6

Ischemic Brain Damage—Enhancement of Protective Effect of Aspirin by 1-Deprenyl

Figure 10:
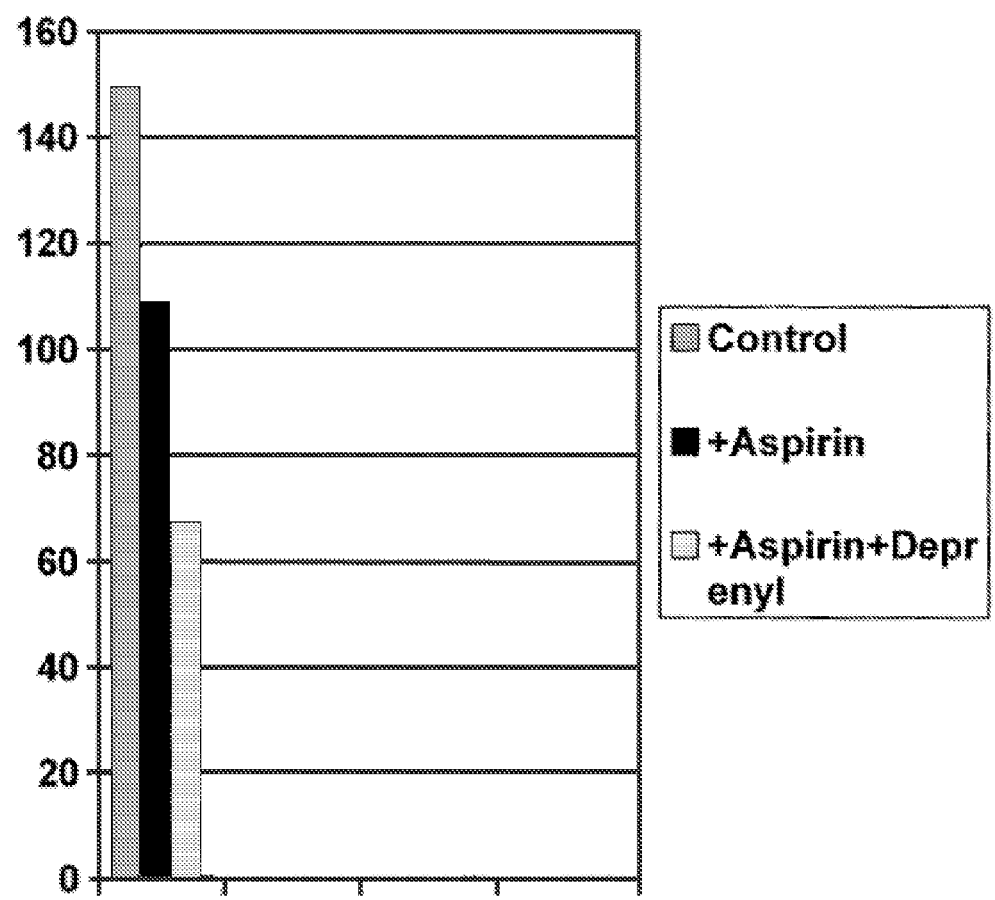
FIG. 10 is a bar graph showing the effect of 1-deprenyl on infarct volume within a rat brain. Rats were pretreated with aspirin, aspirin and 1-deprenyl, or did not receive any treatments. The rats underwent middle cerebral artery occlusion surgery. The rats were euthanized and infarct volumes measured, in cubic mm.

The effect of 1-deprenyl on stroke was further analyzed by measuring infarct volume after middle cerebral artery occlusion (MCAO). Rat models were separated into groups based on treatment for control (no treatment), aspirin, and aspirin and 1-deprenyl treatment. MCAO was surgically induced in rats, as discussed. MCAO produced significant cerebral damage in the control, as seen in FIG. 10. However, pretreating the mouse with aspirin reduced infarct size about 30%. The combination of aspirin and 1-deprenyl further reduced infarct size an additional 36%, to about 48% of the untreated infarct size, demonstrating that the addition of 1-deprenyl reduces brain damage.

The results show a novel antiplatelet activity of 1-deprenyl and other MAO inhibitors. Various agonists trigger platelet aggregation by activation of platelet receptors and modulation of intracellular messengers. L-deprenyl inhibited the platelet aggregation induced by a number of agonists, such as ADP, collagen, arachidonic acid and epinephrine. This indicated that 1-deprenyl influences the activities of a variety of molecules involved in platelet aggregation. The two MAO-B inhibitors currently approved for clinical use, 1-deprenyl and rasagline, both inhibited platelet aggregation and have an in vivo effect on human platelets. Due to drug resistance, many patients taking aspirin and clopidogrel are still at risk for cardiovascular events. Further, alternative pathways involved in platelet aggregation limit the effectiveness of these drugs. L-deprenyl enhanced antiplatelet activities of the major antithrombic drugs and was effective in inhibiting platelet aggregation in patients resistant to aspirin and clopidogrel.

Figure 11:
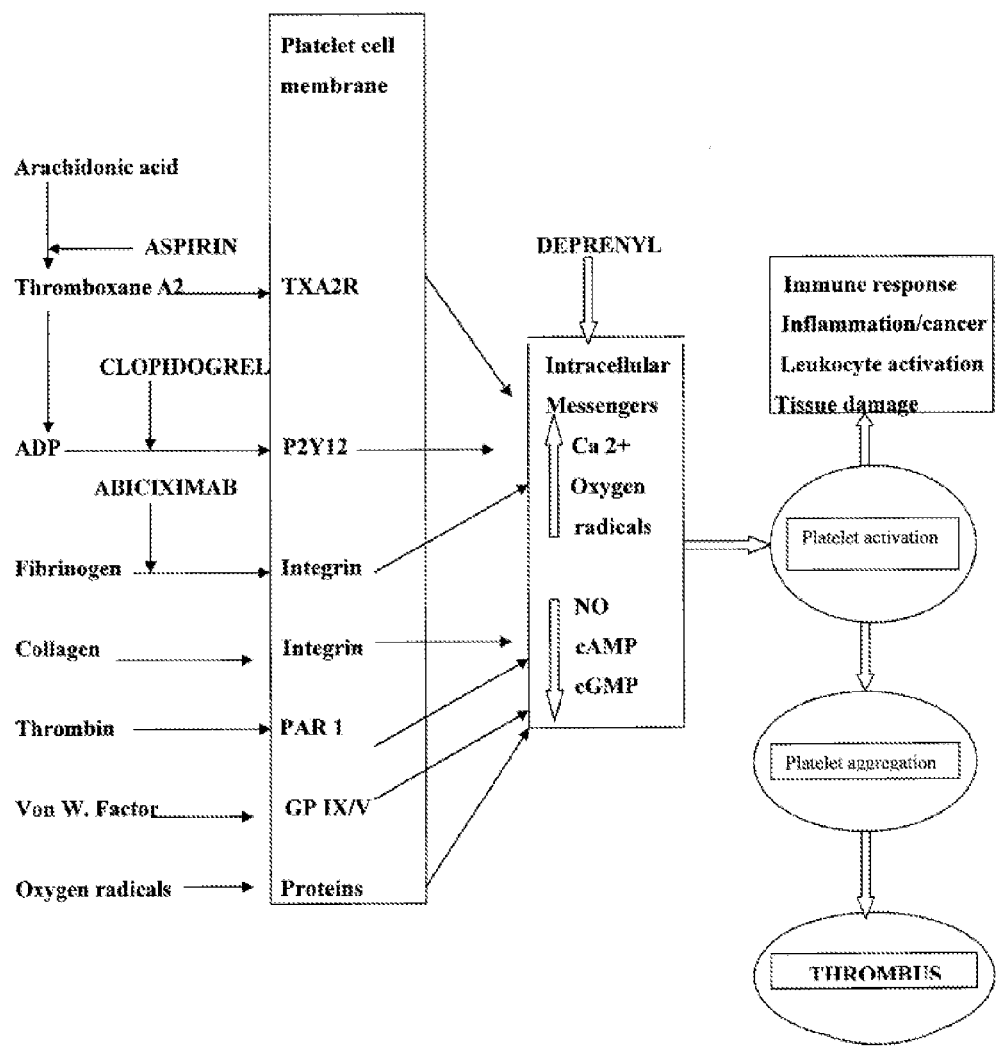
FIG. 11 is a schematic diagram indicating the major action sites for antiplatelet drugs. Multiple agonists and various pathways are involved in regulating platelet function. Currently available drugs like aspirin, clopidogrel and abiciximab inhibit specific pathways. These drugs do not block other alternate pathways. Platelet activating agonists exert their action through intracellular messengers (calcium, oxygen radicals, nitric oxide, cAMP or cGMP). Deprenyl may inhibit platelet aggregation mainly through the effect on intracellular messengers.

Multiple agonists and pathways are involved in regulating platelet function, as seen in FIG. 11. Currently available drugs, like aspirin, clopidogrel, and abiciximab inhibit specific pathways, and cannot block alternate pathways. It has been shown that platelets have the ability to switch aggregation pathways, resulting in resistances to these drugs and limiting the use of the drugs.

L-deprenyl activity is mediated through a variety of mechanisms, such as reduced calcium ion transport, antioxidant activity, increased NO and cAMP or cGMP and effects on agonist receptors, seen in FIG. 11. L-deprenyl prevented formation of platelet thrombus, which occlude blood flow and lead to ischemia. When 1-deprenyl is administered immediately following thrombus formation, 1-deprenyl reversed the aggregation of preformed platelet aggregates. Blood vessel disruption and bleeding were also reduced following 1-deprenyl administration and prevented brain damage and enhanced the neuroprotective effects of aspirin. Platelet activating agonists exert an action through intracellular messengers, like calcium, oxygen radicals, nitric oxide, cAMP, or cGMP. L-deprenyl and other MAO inhibitors act against platelet aggregation mainly through these intracellular messengers, allowing improved anti-thrombolytic treatments.

Vascular disease (cardiovascular disease, cerebrovascular disease, and peripheral vascular disease) is the major cause of morbidity and morality worldwide. Pharmacological interventions to prevent platelet aggregation, ensuring adequate blood supply, have been a major therapeutic option in the treatment and prevention of vascular disease. Antiplatelet agents, such as aspirin, thienopyridines, and platelet glycoprotein IIb/IIIa receptors have become the cornerstone of antithrombitic therapy. Despite aspirin's ability to reduce the risk of adverse thrombotic events, it has a variable antiplatelet activity in individuals and aspirin resistance in a large segment of patients is a major concern. Platelet aggregation involves alternative pathways not blocked by aspirin. Thus, addition of other drugs to target these alternative pathways has been used to complement the therapeutic effect of aspirin. Addition of thienopyridines (clopidogrel or prasugrel) and platelet glycoprotein IIb/IIIa receptor antagonists (abiciximab) are widely used to enhance the antiplatelet effect of aspirin. However, some patients are resistant to these drugs, and increased bleeding associated with duel antiplatelet therapy and the high cost of treatment has prompted the search for other avenues of enhancing the efficacy of aspirin. The ability of 1-deprenyl to prevent platelet aggregation and cause dissolution of a thrombus plug shows that it may be used to reestablish blood flow in occluded vessels, reducing ischemic damage. L-deprenyl and other MAO inhibitors were found to prevent platelet aggregation and augment the antiplatelet activity of aspirin and clopidogrel in human and animal studies. As such, 1-deprenyl may be used as a therapeutic agent for cardiovascular disease, cerebrovascular disease, or peripheral vascular disease by virtue of its antithrombotic, antioxidant, and anti-inflammatory properties and provides a safe, affordable alternative to current antiplatelet therapies.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention that, as a matter of language, might be said to fall therebetween. Now that the invention has been described,

What is claimed is:

1. A method of preventing or treating myocardial infarction by inhibiting platelet reactivity, comprising the step of;
   administering a therapeutically effective amount of a composition, wherein the composition comprises at least one monoamine oxidase B inhibitor, wherein the at least one monoamine oxidase B inhibitor is 1-deprenyl, rasagiline, or propargylamine; and
   an antithrombotic agent, wherein the antithrombotic agent is clopidogrel, aspirin, or a salt thereof.

2. The method of claim 1, wherein the at least one monoamine oxidase inhibitor is 1-deprenyl.

3. The method of claim 1, wherein the monoamine oxidase B inhibitor is administered by the route selected from the group consisting of oral, intravenous, intra-arterial, intra-articular, intra-cerebral, subcutaneous, transcutaneous, intraperitoneal, intraspinal, intrarectal, transcutaneous, intramuscular, and intranasal.

4. The method according to claim 2, wherein the amount of 1-deprenyl is administered at about 0.1 mg to 500 mg per day.

5. The method of claim 1, where the antithrombotic agent is clopidogrel, or clopidogrel bisulfate.

6. A method for preventing or treating myocardial infarction by inhibiting platelet reactivity, comprising the step of:
   administering a therapeutically effective amount of composition, wherein the composition comprises a monoamine oxidase B inhibitor, wherein the monoamine oxidase B inhibitor is 1-deprenyl or rasagiline; and
   an antithrombotic agent, wherein the antithrombotic agent is clopidogrel or aspirin.

7. The method of claim 6, wherein the monoamine oxidase inhibitor is administered by the route selected from the group consisting of oral, intravenous, intra-arterial, intra-articular, intra-cerebral, subcutaneous, transcutaneous, intraperitoneal, intraspinal, intrarectal, transcutaneous, intramuscular, and intranasal.

8. A method of preventing or treating myocardial infarction by inhibiting platelet reactivity, comprising the step of;
   administering a therapeutically effective amount of at least one antithrombotic agent and at least one monoamine oxidase B inhibitor,
   wherein the at least one monoamine oxidase B inhibitor comprises:

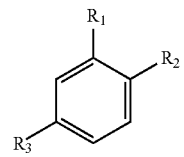

wherein $R_1$ is H or forms a pentacyclic compound with $R_2$;
   $R_2$ is $CH_2CH(CH_3)N(CH_3)CH_2CCH$, or forms a pentacyclic compound with $R_1$;
   where the pentacyclic compound formed by $R_1$ and $R_2$ is $CH2CH2CH(NHCH_2CCH)$;
   $R_3$ is H, or Cl; and
   wherein the at least one antithrombotic agent is clopidogrel, clopidogrel bisulfate, or aspirin.

9. The method of claim 8, wherein the at least one monoamine oxidase inhibitor is selected from the group consisting of 1-deprenyl, or rasagiline.

10. The method of claim 8, wherein the monoamine oxidase B inhibitor is administered by the route selected from the group consisting of oral, intravenous, intra-arterial, intra-articular, intra-cerebral, subcutaneous, transcutaneous, intraperitoneal, intraspinal, intrarectal, transcutaneous, intramuscular, and intranasal.

11. The method according to claim 9, wherein the amount of 1-deprenyl is administered at about 0.1 mg to 500 mg per day.

12. The method of claim 8, wherein the antithrombotic agent is aspirin.

13. The method of claim 8, where the antithrombotic agent is clopidogrel, or clopidogrel bisulfate.

* * * * *